United States Patent [19]

Tseng et al.

[11] Patent Number: 5,013,737
[45] Date of Patent: May 7, 1991

[54] 2,4,8-TRISUBSTITUTED-3H,6H-1,4,5A,8A-TETRAAZAACENAPHTYLENE-3,5-(4H)-DIONES AND 2,4-8-TRISUBSTITUTED-4,5-DIHYDRO-5-THIOXO-3H,6H-1,4,5A,8A-TETRAZAACENAPHTHYLEN-3-ONES

[75] Inventors: Shin S. Tseng, Bridgewater, N.J.; Joseph W. Epstein, Monroe; Jeremy I. Levin, Spring Valley, both of N.Y.

[73] Assignee: American Cyanamid Company, Stamford, Conn.

[21] Appl. No.: 482,568

[22] Filed: Feb. 21, 1990

Related U.S. Application Data

[63] Continuation-in-part of Ser. No. 278,296, Nov. 30, 1988, Pat. No. 4,916,147, which is a continuation-in-part of Ser. No. 158,448, Feb. 22, 1988, abandoned.

[51] Int. Cl.$^5$ .................. A61K 31/505; C07D 239/00
[52] U.S. Cl. ..................................... 514/267; 544/251
[58] Field of Search .......................... 544/251; 514/267

[56] References Cited

U.S. PATENT DOCUMENTS

| | | | |
|---|---|---|---|
| 4,178,449 | 12/1979 | Dusza et al. | 544/281 |
| 4,236,005 | 11/1980 | Dusza et al. | 544/281 |
| 4,281,000 | 7/1981 | Dusza et al. | 544/281 |
| 4,614,732 | 9/1986 | Hamilton et al. | 514/46 |
| 4,713,383 | 12/1987 | Francis et al. | 514/267 |

*Primary Examiner*—Mary C. Lee
*Assistant Examiner*—Robert C. Whittenbaugh
*Attorney, Agent, or Firm*—H. G. Jackson

[57] ABSTRACT

Novel 2,4,8-trisubstituted-3H,6H-1,4,5a,8a-tetraazaacenaphthylene-3,5 (4H)-diones and 2,4,8-trisubstituted-4,5-dihydro-5-thioxo-3H, 6H-1,4,5a,8a-tetraazaacenaphthylen-3-ones are disclosed which are useful antihypertensive and anxiolytic agents.

26 Claims, No Drawings

2,4,8-TRISUBSTITUTED-3H,6H-1,4,5A,8A-TETRAAZAACENAPHTYLENE-3,5-(4H)-DIONES AND 2,4-8-TRISUBSTITUTED-4,5-DIHYDRO-5-THIOXO-3H,6H-1,4,5A,8A-TETRAZAACENAPHTHYLEN-3-ONES

The present application is a continuation-in-part of U.S. Pat. application Ser. No. 07/278,296, filed Nov. 30, 1988, now U.S. Pat. No. 4,916,137, which is in turn a continuation in part of U.S. Pat. application Ser. No. 07/158,448, filed Feb. 22, 1988, now abandoned.

The present invention relates to novel organic compounds and more particularly relates to novel 2,4,8-trisubstituted-3 H,6H-1,4,5a,8a-tetraazaacenaphthylene-3, 5-(4H)-diones and 2,4,8-trisubstituted-4,5-dihydro-5-thioxo-3H,6H-1,4,5 a,8a-tetraazaacenaphthylen-3-ones, which are useful as antihypertensive agents and/or agents for the treatment of cognitive and related neural behavioral problems in mammals and as intermediates.

BACKGROUND OF THE INVENTION

It is known in the art to employ organic compounds as antihypertensive agents and/or as agents for the treatment of cognitive and related neural behavioral problems in mammals.

Dusza et al., U.S. Pat. No. 4,236,005 disclose substituted pyrazolo(1,5-a) pyrimidines (I) and imidazo (1,5-a) pyrimidine (II) compounds of the formulae:

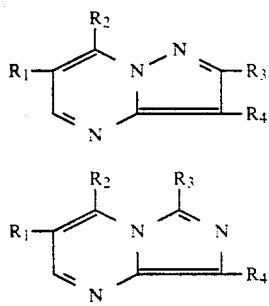

wherein $R_1$ is hydrogen or alkyl having from 1 to 3 carbon atoms; $R_2$ is selected from the group consisting of phenyl, ortho-trifluoromethylphenyl, meta-trifluoromethylphenyl and meta-methoxyphenyl; $R_3$ is hydrogen, fluoro, chloro, bromo, cyano, cyanomethyl, carbamoyl or alkyl having from 1 to 3 carbon atoms; and $R_4$ is selected from the group consisting of hydrogen, fluoro, chloro, bromo, formyl, carboxyl, cyano, hydroxymethyl, N-hydroxyformimidoyl, alkyl having from 1 to 3 carbon atoms,

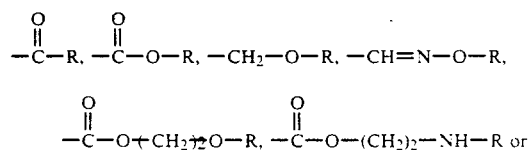

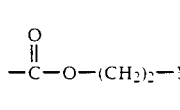

wherein R is alkyl having from 1 to 3 carbon atoms; which possess central nervous system activity and are useful as anxiolytic agents.

Dusza, et al., U.S. Pat. No. 4,281,000, disclose pyrazolo(1,5-a)pyrimidine compounds of the formula:

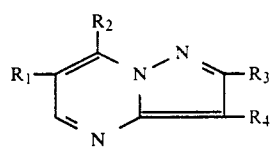

wherein $R_1$ is hydrogen or alkyl having from 1 to 3 carbon atoms; $R_2$ is selected from the group consisting of

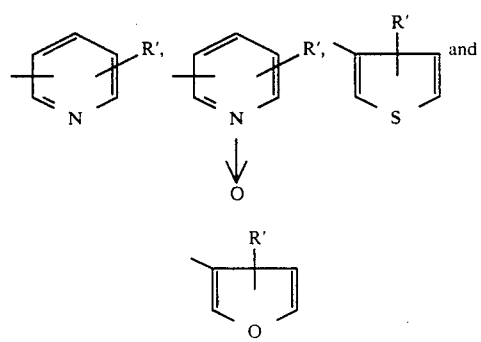

wherein R' is hydrogen or alkyl having from 1 to 3 carbon atoms; $R_3$ is hydrogen, fluoro, chloro, bromo, cyano, cyanomethyl, carbamoyl or alkyl having from 1 to 3 carbon atoms; $R_4$ is selected from the group consisting of hydrogen, fluoro, chloro, bromo, formyl, carboxyl, cyano, hydroxymethyl, N-hydroxyformimidoyl, alkyl having from 1 to 3 carbon atoms,

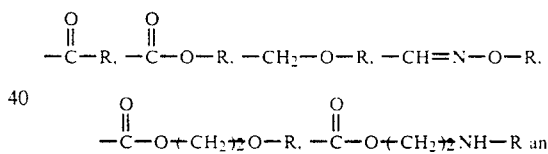

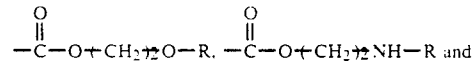

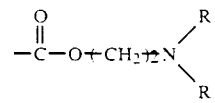

wherein R is alkyl having from 1 to 3 carbon atoms; which possess anxiolytic activity.

Dusza et al., U.S. Pat. No. 4,178,449 describe substituted pyrazolo(1,5-a) pyrimidines and imidazo(1,5-a) pyrimidines of the formula

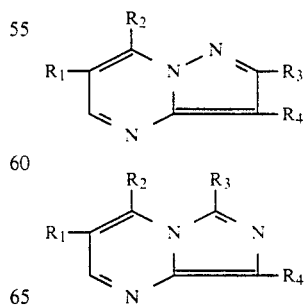

wherein $R_1$, $R_2$, $R_3$ and $R_4$ are as defined in relation to formulae (I) and (II); which possess anxiolytic activity.

Epstein et al., U.S. Pat. application Ser. No. 07/278,296, filed Nov. 30, 1988, now allowed, disclose compounds of the formula

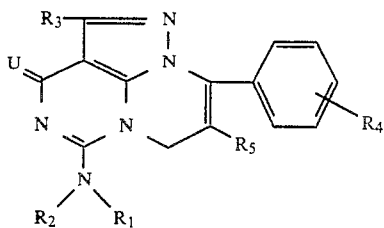

wherein $R_1$ and $R_2$ are each individually selected from the group consisting of hydrogn, alkyl $(C_1-C_4)$, benzoyl, mono or dissubstituted benzoyl wherein the substituents are alkyl $(C_1-C_6)$, alkoxy $(C_1-C_6)$, acyloxy $(C_2-C_7)$, halogen, nitro or trifluoromethyl, and moieties of the formulae

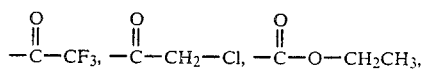

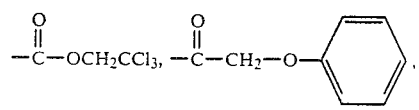

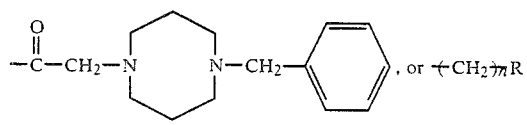

wherein n is an integer from 1 to 3 and R is hydroxy, 4-morpholinyl, 1H-imidazol-1-yl, —CH(alkoxy($C_1-C_3$))$_2$, α-hydroxybenzyl, phenyl or mono or disubstituted phenyl wherein the substitutents are halogen or alkyl $(C_1-C_6)$; $R_1$ and $R_2$ taken together with their associated nitrogen is 4-morpholinyl or a moiety of the formula —N(CH$_2$)m wherein m is an integer of 2 to 6; $R_3$ is hydrogen or alkyl $(C_1-C_6)$ $R_4$ is hydrogen, halogen, alkoxy $(C_1-C_3)$, alkyl $(C_1-C_3)$ or trifluoromethyl; and $R_5$ is hydrogen or alkyl $(C_1-C_6)$; which are useful in the treatment of cognitive and related neural behavioral disorders in warm blooded animals.

Francis et al. U.S. Pat. No. 4,713,387 disclose triazoloquinazoline compounds of the formula

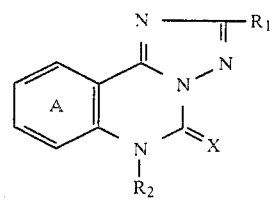

wherein $R_1$ is optionaly substituted phenyl, pyridyl, furyl thienyl, dihydro or tetrahydrofuranyl or thienyl, pyranyl, or O-ribofuranosyl; $R_2$ is hydrogen or lower alkyl; X is oxygen, sulfur or $NR_3$ where $R_3$ is hydrogen, lower alkyl, aryl-lower alkyl, cycloalkyl, lower alkenyl in which the unsaturated bond is separated from the nitrogen atom by at least one saturated carbon atom, lower alkynyl in which the unsaturated bond is separated from the nitrogen by at least one saturated carbon atom, aryl, amino-lower alkyl, lower alkylamino-lower alkyl, di-lower alkylamino-lower alkyl or hydroxy-lower alkyl; and Ring A is unsubstituted or substituted by lower alkyl, lower alkoxy, hydroxy, halogen, trifluoromethyl, nitro, amino, lower alkyl thio, lower alkyl sulfonyl, lower alkyl sulfinyl or aryl-lower alkoxy; which are useful as adenosine antagonists and benzodiazepine antagonists.

Also to be mentioned is Hamilton et al., U.S. Pat. No. 4,614,732 which discloses $N^6$-acenaphthyl adenosines and analogs thereof useful in lowering blood pressure in mammals.

None of the above patents disclose the novel 2,4,8-trisubstituted-3H,6H-1,4,5a,8a-tetraazaacenaphthylene-3,5-(4H)diones and 2,4,8-trisubstituted-4,5-dihydro-5-thioxo-3H,6H-1,4,5a,8a-tetraazaacenaphthylene-3-ones of the present invention. Surprisingly the dione compounds of the present invention possess anti-hypertensive activity and are useful as agents in the treatment of cognitive and related neural behavioral problems in mammals; and the 5-thioxo compounds are useful as intermediates and in the treatment of cognitive and related neural behavioral problems in mammals.

SUMMARY OF THE INVENTION

According to the present invention there are provided compounds selected from the group consisting of those of the formula (III)

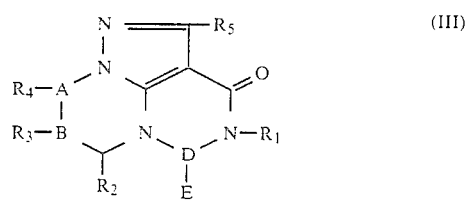

wherein $R_1$ is selected from the group consisting of hydrogen, alkyl having from 1 to 10 carbon atoms, carboxamidomethyl, 4-chlorophenyl, benzyl and (4-nitrophenyl)methyl; $R_2$ and $R_3$ may be hydrogen or alkyl having from 1 to 3 carbon atoms; $R_4$ is

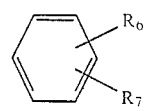

where $R_6$ and $R_7$ may be the same or different and are selected from hydrogen, halogen, alkyl having from 1 to carbon atoms, alkoxy having from 1 to 3 carbon atoms, N-alkyl-N-acylamino, where both alkyl and acyl have from 1 to 3 carbon atoms; nitro and trifluoromethyl; and where halogen is selected from chlorine, bromine, fluorine and iodine; $R_4$ may also be 3-pyridinyl; $R_5$ is hydrogen or alkyl having from 1 to 10 carbon atoms; A-B is

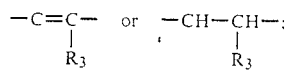

D-E represents C=X where X is oxygen or sulfur, or C—SR$_8$ where R$_8$ is alkyl having from 1 to 3 carbon atoms.

Preferably, the compound is selected from the group consisting of those of the formula:

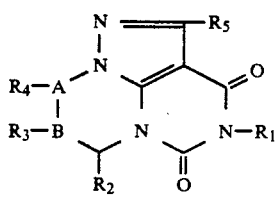

wherein $R_1$ is selected from the group consisting of hydrogen, alkyl having from 1 to 10 carbon atoms, carboxamidomethyl, 4-chlorophenyl, benzyl and (4-nitrophenyl)methyl; $R_2$ and $R_3$ are hydrogen or alkyl having from 1 to 3 carbon atoms; $R_4$ is 3-pyridinyl or

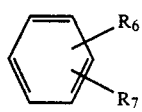

where $R_6$ and $R_7$ may be the same or different and are selected from hydrogen, halogen, alkyl having from 1 to 3 carbon atoms, alkoxy having from 1 to 3 carbon atoms, N-alkyl-N-acylamino where both alkyl and acyl have from 1 to 3 carbon atoms, nitro and trifluoromethyl; where halogen is selected from chlorine, bromine, fluorine and iodine; $R_5$ is hydrogen or alkyl having from 1 to 10 carbon atoms; and A-B is

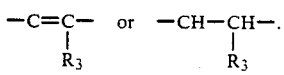

Especially preferred compounds are 7-(3-(trifluoromethyl)phenyl)-3H,6H-1,4,5a,8 a-tetraazaacenaphthylene-3,5(4H)-dione; 7,8-dihydro-8-(3-trifluoromethyl)phenyl-3H,6H-1,4,5a,8a-tetraazaacenaphthylene-3,5 (4H)-dione; 8-(2,5-dichlorophenyl)-2-methyl-3H,6H-1,4,5a, 8a-tetraazaacenaphthylene-3,5(4H)-dione; 4-methyl-8-(3-trifluoromethyl)phenyl)-3H,6H-1,4,5a,8a-tetraazaacenaphthylene-3,5(4H)-dione; 8-(3-pyridinyl)-3H,6H-1,4,5a, 8a-tetraazaacenaphthylene-3,5(4H)-dione; 4-(4-chlorophenyl)-8-(3-(trifluoromethyl)phenyl)-3H,6H-1,4,5a,8a-tetraazaacenaphthylene-3,5(4H)-dione; 3,5-dioxo-8-(3-trifluoromethyl)phenyl)-3H,6H-1,4,5a,8a-tetraazaacenaphthylene-4 (5H)-acetamide; 4-ethyl-8-(3-(trifluoromethyl)phenyl)-3H,6H-1,4,5a,8a-tetraazaacenaphthylene-3, 5(4H)-dione; 4-((4-nitrophenyl)methyl)-8-(3-(trifluoromethyl)phenyl)-3H,6H,-1,4,5a,8a-tetraazaacenaphthylene-3, 5(4H)-dione; and 4-(phenylmethyl)-8-(3-trifluoromethyl) phenyl)-3H,6H-1,4,5a,8a-tetraazaacenaphthylene-3,5(4H)-dione.

Also, according to the present invention, there are provided novel compositions of matter containing the compounds whiih are useful as antihypertensive agents and as nootropic agents in mammals, and the methods for treating hypertension, and cognitive and related neural behavioral problems in mammals therewith. Further, according to the present invention, there are provided processes for the production of the compounds of the present invention.

DETAILED DESCRIPTION OF THE INVENTION

The present invention discloses novel organic compounds, and more particularly is concerned with novel 2,4,8-trisubstituted-3H,6H-1,4,5a,8a-tetraazaacenaphthylene-4,5-dihydro-5-oxo and 5-thioxo-3H,6H-1,4,5a,8a-tetraazaacenaphthylen-3-ones which are useful as antihypertensive agents and/or as agents for the treatment of cognitive and related neural behavioral problems in mammals.

Certain of the compounds of the present invention also have utility as intermediates for the preparation of their alkylated analogs.

The novel compounds of the present invention are in general obtainable as white to pale yellow crystalline solids having characteristic melting points and absorption spectra. They are generally soluble in organic solvents such as lower alkanols, acetonitrile, chloroform, dichloromethane, N,N-dimethylformamide, dioxane, toluene and the like, but are generally insoluble in water.

The novel 2,4,8-trisubstituted-4,5-dihydro-5-oxo and 5-thioxo-3H,6H-1,4,5a,8a-tetraazaacenaphthylene-3-ones of the present invention may be readily prepared as set forth in the following general reaction schemes:
(a) reacting a compound of the formula

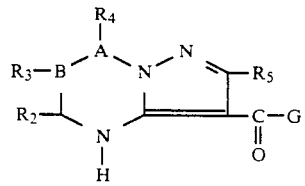

where $R_2$, $R_3$, $R_4$, $R_5$ and A-B are as defined above in formula (III) and G is ethyl ester (OEt) or $NH_2$ with; either (b)(i) a compound of the formula $R_1$—NCO where G is ethyl ester and $R_1$ is as above defined in formula (III) to produce a compound of the formula

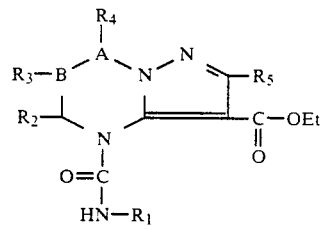

where $R_1$, $R_2$, $R_3$, $R_4$, $R_5$ and A-B are as above defined and OEt represents ethyl ester, and (b)(ii) reacting the product of step (b)(i) with a base to produce a compound of the formula

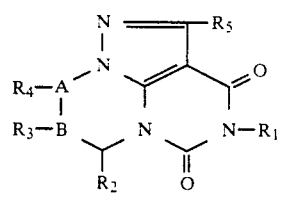

where $R_1$, $R_2$, $R_3$, $R_4$, $R_5$ and A-B are as above defined;
or
(c) a compound of the formula

where Z is

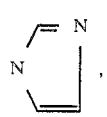

Cl or methoxy and X is oxygen or sulfur; either
(d)(i) in an inert solvent, where X is oxygen, to obtain a compound of the formula

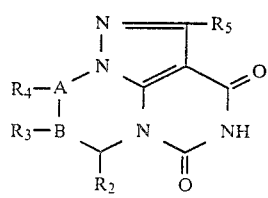

where $R_2$, $R_3$, $R_4$, $R_5$ and A-B are as defined above; and
(d)(ii) reacting the product of step (d)(i) with an alkylating agent to obtain a compound of the formula

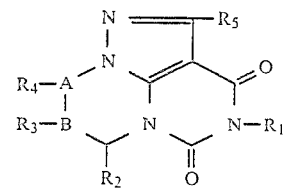

where $R_1$, $R_2$, $R_3$, $R_4$, $R_5$ and A-B are as defined above;
or
(e)(i) with a base, where X is sulfur, to obtain a compound of the formula

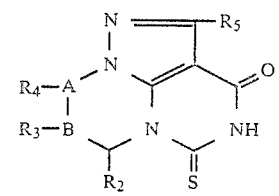

where $R_2$, $R_3$, $R_4$, $R_5$ and A-B are as defined above; and
(e)(ii) reacting the product of step (e)(i) with an alkylating agent to produce a compound of the formula:

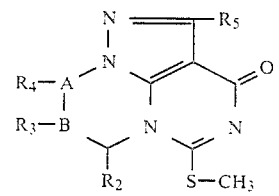

wherein $R_2$, $R_3$, $R_4$, $R_5$ and A-B are as defined above.

In a preferred embodiment, the compounds of the present invention may be obtained by the following process:

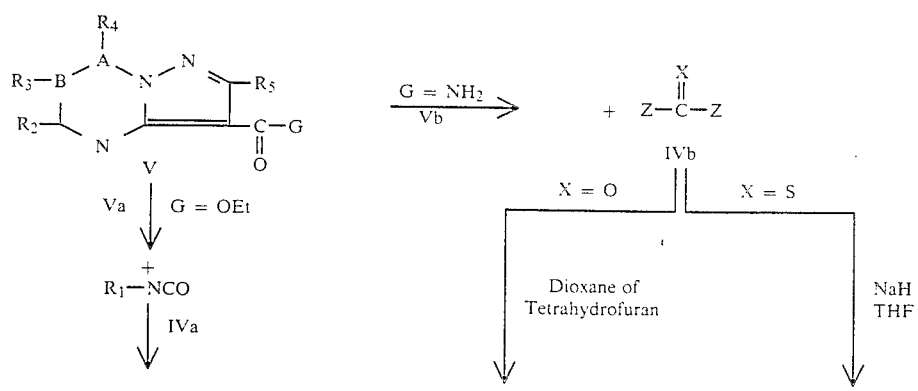

-continued

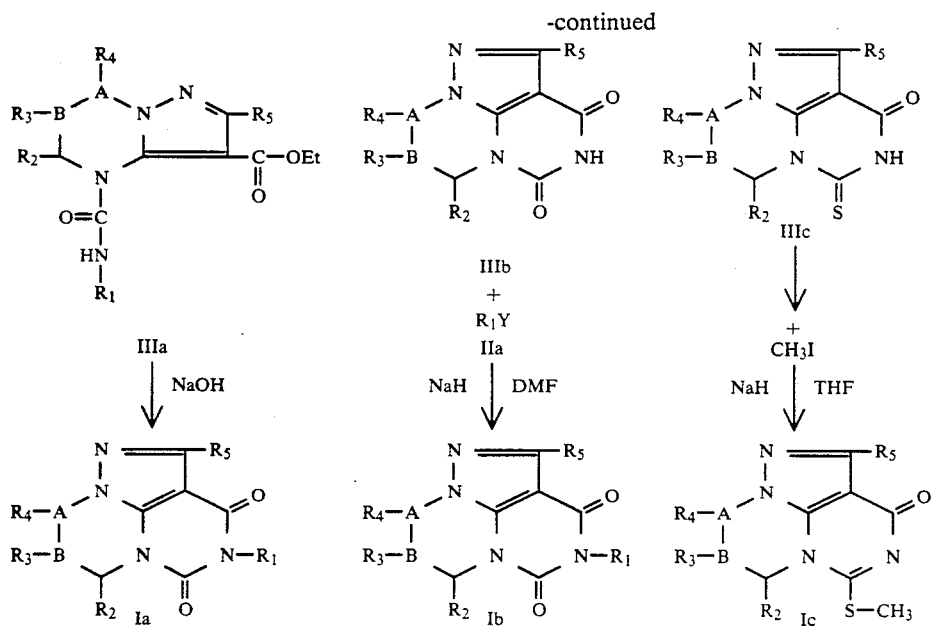

wherein $R_1$, $R_2$, $R_3$, $R_4$, $R_5$ and A-B are as above defined in formula (III), X is oxygen or sulfur, G is $NH_2$ or ethyl ester (OEt), Y is bromine or iodine and Z is

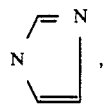

chlorine or methoxy.

As shown hereinabove, (1) a 2,7-disubstituted 4,5-dihydro, or 4,5,6,7-tetrahydropyrazolo(1,5-a) pyrimidine-3-carboxylic acid, ethyl ester (Va) (prepared as described in commonly assigned U.S. Pat. No. 4,178,449) is reacted with a substituted isocyanate of the formula $R_1$-NCO (IVa), where $R_1$ is as above defined, in an inert solvent, such as toluene, by heating at the reflux temperature for 4-96 hours to obtain the corresponding 4-substituted aminocarbonyl-4,5-dihydro or 4,5,6,7-tetrahydropyrazolo(1,5-a)pyrimidine-3-carboxylic acid, ethyl ester (IIIa). The 4-substituted-aminocarbonyl, ethyl ester (IIIa) is then reacted with a base, such as sodium hydroxide, with stirring at about 120° C. for 2 to 5 hours. The reaction mixture is then allowed to cool to room temperature. The solid which forms is collected, and washed with water followed by glacial acetic acid, and then dried in vacuo to give the 2,4,8-trisubstituted 3H,6H-1,4,5a,8a-tetraazaacenaphthylene-3,5-(4H)diones the 7,8-dihydro-2,4,8-trisubstituted-3H,6H-1,4,5a,8a-tetraazaacenaphthylene-3,5(4H)-diones (Ia).

Alternatively, (2) a 2,7-disubstituted 4,5-dihydro, or 4,5,6,7-tetrahydropyrazolo(1,5-a)pyrimidine 3-carboxamide (Vb) (prepared by the reduction of a pyrazolo(1,5-a)pyrimidine in the manner described in Tseng et al., U.S. Pat. No. 4,847,256) is reacted with 1,1'-carbonyldiimidazole, phosgene, or dimethyl carbonate and the like (IVb), under nitrogen in an inert solvent, such as p-dioxane or tetrahydrofuran, by heating at the reflux temperature for 4-96 hours to obtain the corresponding 2,8-disubstituted-3H,6H-1,4,5a, 8a-tetraazaacenaphthylene-3,5(4H)-dione or the 7,8-dihydro-2,8-disubstituted-3H,6H 1,4,5a,8a-tetraazaacenaphthylene-3,5(4H)-dione (IIIb). The dione (IIIb) may then be alkylated under nitrogen, at room tmmperature, in a solvent such as N,N-dimethylformamide and the like, using sodium hydride as the base with an alkylating agent (IIa), such as methyl iodide, 2-iodoacetamide, iodoethane, 4-nitrobenzyl bromide or benzyl bromide and the like for 6-60 hours. Evaporation of the solvent gives a solid which is washed with water, filtered and purified in a conventional manner using solvents such as chloroform, dichloromethane, ether, hexane, acetonitrile, N,N-dimethylformamide and the like to give the 2,4,8-tri-substituted-3H,6H-1,4,5a,8a-tetraazaacenaphthylene-3,5-(4H)-diones or the 7,8-dihydro-2,4,8-trisubstituted-3H, 6H-1,4,5a,8a-tetraazaacenaphthylene-3,5(4H)-diones (Ib). (3) Or the reduced pyrazolo(1,5-a)pyrimidine-3-carboxamide (Vb) in an inert solvent such as dry tetrahydrofuran or p-dioxane and the like, is stirred with sodium hydride under nitrogen at a temperature of about $-78°$ C. for 20 minutes to 3 hours. Then 1,1'-thiocarbonyldiimidazole (IVb) is added and the reaction mixture is stirred in the cold for 1-3 hours and then allowed to warm to room temperature. After being stirred for 24-48 hours at room temperature, the reaction is then quenched with water and the mixture is neutralized with 5 percent aqueous hydrochloric acid. The 4,5-dihydro-5-thioxo-3H, 6H-1,4,5a,8a-tetraazaacenaphthylen-3-one (IIIc) is recovered by precipitation or by extraction with a solvent such as chloroform and the like, followed by evaporation of the solvent. The 5-thioxo compound (IIIc) in tetrahydrofuran is stirred with a base such as sodium hydride at 0° C. for about 15 minutes, then is treated with an excess of an alkyl halide such as methyl iodide, ethyl iodide or ethyl bromide. The reaction mixture is allowed to warm to room temperature with stirring for 3 hours. The mixture is quenched with water and extracted into a solvent such as chloroform and the like. Evaporation of the solvent gives the 5-alkyl-thio-8-substituted-3H,6H-1,5a,8a-tetraazaacenaphthylen-3-one, compound (Ic).

The 4,5-dihydropyrazolo(1,5-a)pyrimidine intermediate compounds were, in general, prepared as follows: A pyrazolo(1,5-a)pyrimidine with a hydrogen, phenyl, substituted phenyl, or heteroaryl group in the C-7 position and an electron withdrawing group in the C-3 position was reacted with sodium cyanoborohydride by stirring in glacial acetic acid under an inert atmosphere in an ice bath for about one hour, then at room temperature for from 1 to 12 hours and the resulting precipitate collected and washed with water. The solid was dissolved in an inert solvent such as dichloromethane or acetonitrile and the like and washed with saturated sodium bicarbonte. Separation and evaporation of the organic phase gave the crude dihydro product which was recrystallized from a solvent such as isopropyl alcohol or acetonitrile and the like or a mixture of solvents such as ether-hexane, chloroform-methanol or N,N-dimethylformamide-acetonitrile and the like.

When the dihydro product was reduced with triethylsilane in trifluoroacetic acid at 60° C. for 1–24 hours according to the procedure of Lanzilotti, et al., J. Org. Chem., 44, 4809 (1979) and the reaction mixture at ambient temperature was made slightly basic (pH 9) with aqueous potassium hydroxide the 4,5,6,7-tetrahydropyrazolo(1,5-a)pyrimidine product was precipitated, then isolated and purified by crystallization or chromatography.

The pyrazolo(1,5-a)pyrimidines are disclosed in U.S. Pat. Nos. 4,178,449; 4,236,005; 4,281,000 and 4,521,422. They are prepared by condensation of 3-aminopyrazoles and substituted 3-aminopyrazoles with 1,3-carbonyl compounds as described in J. Med. Chem., 18, 645 (1974); J. Med. Chem., 18, 460 (1975); J. Med. Chem., 20, 386 (1977); Synthesis, 673 (1982); and references contained therein.

It has been found that the use of sodium cyanoborohydride in acetic acid offers a simple, convenient, regioselective means for the reduction of pyrazolo(1,5-a)pyrimidines and derivatives thereof, bearing functional groups such as halogens, nitriles, amides, amidines, esters, carboxylic acids and aryl ketones, without reducing these groups, and providing the final products in higher yield than obtained with other reducing agents. In fact, certain of the above described functional groups are known to be affected by other reducing agents, with mixtures of products being formed which require the employment of time consuming separation techniques to obtain the desired product.

In certain instances the reduction of pyrazolo(1,5-a)pyrimidine derivatives with sodium cyanoborohydride in glacial acetic acid results in reduction to the tetrahydro derivative, along with the dihydro product.

Another effective means for the reduction of pyrazolo(1,5-a)pyrimidines is concerned with the utilization of sodium borohydride in glacial acetic acid. This method although effective does not provide yields commensurate with those obtained by the use of sodium cyanoborohydride. This difference could be due to the fact that sodium cyanoborohydride is more stable in glacial acetic acid than is sodium borohydride although the inventor does not wish to be bound by any theory. It has also been discovered that when sodium borohydride is reacted with a pyrazolo(1,5-a)pyrimidine derivative such as 7-(4-chlorophenyl)-5-methylpyrazolo(1,5-a)pyrimidine-3-carbonitrile or 7-(3-chlorophenyl)-5-methylpyrazolo(1,5-a)pyrimidine-3-carbonitrile in tetrahydrofuran:methanol (1:1) by stirring at room temperature for 24 hours or at 55° C. for 6 hours the corresponding tetrahydro compound is obtained.

Still another means for the reduction of pyrazolo(1,5-a)pyrimidines or further reduction of 4,5-dihydropyrazolo(1,5-a)pyrimidines to the 4,5,6,7-tetrahydro form resides with the catalytic hydrogenation of the compound by shaking in a suitable apparatus, such as a Parr shaker, with a solvent such as ethyl acetate, N,N-dimethylformamide, or the like in the presence of a catalyst such as 10 percent palladium on carbon under an initial hydrogen pressure of from 5 to 30 lbs until the uptake of hydrogen is complete, followed by separation and purification of the reduction product by conventional means.

The novel compounds of the present invention are active hypotensive agents at nontoxic doses when administered to mammals. These compounds were tested for hypotensive activity by the method of P.S. Chan and D.W. Poorvin, Clinical and Experimental Hypertension, 1 (6), 817–830 (1979). Male, 16 week old, spontaneously hypertensive rats of the Okamoto strain having an average mean arterial blood pressure of 160±1.5 mm of mercury are used in the test. One to three rats are used per test compound. A rat is dosed by gavage with a test compound, suspended in 2 percent pre-boiled starch at a concentration of 50 mg/ml, at a dose of 100 mg/kg of body weight or less, with 0.9 percent sodium chloride loading at a dose of 25 ml/kg of body weight. A second identical dose of the test compound, without sodium chloride loading is given 24 hours later. At 28 hours after the initial dose the mean arterial blood pressure is measured by the method of Chan and Poorvin vide supra. The procedure is repeated in a second and third rat when necessary.

The results of this test on representative compounds of the present invention appear below in Table I.

TABLE I

| Reduction of Mean Arterial Blood Pressure in Spontaneously Hypertensive Rats | |
|---|---|
| Compound | MABP/mm HG (No. of rats) |
| 8-(3-Pyridinyl)-3H,6H-1,4,5a,8a-tetraazaacenaphthylene-3,5(4H)-dione | 113 (1) |
| 4-Ethyl-8-(3-trifluoromethyl)phenyl)-3H,6H-1,4,5a,8a-tetraazaacenaphthylene-3,5(4H)-dione | 130 (2) |
| 4-((4-Nitrophenyl)methyl)-8-(3-(trifluoromethyl)phenyl)-3H,6H-1,4,5a,8a-tetraazaacenaphthylene-3,5(4H)-dione | 110 (1) |

MABP = mean arterial blood pressure

The novel compounds of the present invention possess the ability to enhance neural function in warm-blooded animals affected by behavioral neurological problems, including the cognitive deterioration associated with decreased neural function which occurs with cerebral insufficiency, aging, dementia.

The Hypoxic Survival test is a useful in vivo test for measuring the effectiveness of central nervous system-acting drugs in enhancing survival in a hypoxic environment relative to the known parasympathomimetic agent physostigmine. This assay shows the enhanced survival of animals in a hypoxic environment after treatment with the drug as compared to saline-treated control animals.

Extensive testing has demonstrated that under conditions of 10 percent oxygen, only 5 to 10 percent of control mice (treated with saline) survive after 5 minutes, whereas 60 to 80 percent of the physostigmine treated mice survice. Drugs are injected interperitoneally to groups of mice 30 minutes prior to placing them in a hypoxic mixture and survival is measured. The rationale of this test is that drugs which enhance survival under hypoxic conditions without concomitmant depression, or sedative side effects, may do so by enhancing brain metabolism, i.e., by improving energy supply relative to demand and so preserving normal brain function under conditions of reduced energy metabolism. Given the dependence of the brain on a constant supply of energy, drugs which have this property may have many far-reaching therapeutic indications, including recovery from stroke and closed head injury, and reducing the deleterious effects of age-related central nervous system deficits. For example, in aged and senile demented people, deficiencies in energy metabolism are thought to contribute significantly to the neurochemical and neurophysiological dysfunctions of aging.

Groups of 20 Royal Hart mice (6 weeks of age) are injected intraperitoneally with test compound (1–200 mg/kg) 30 minutes prior to placing them in a hypoxic mixture (10 percent oxygen in 90 percent carbon dioxide) and measuring survival after 5 minutes.

A separate group of 20 mice is injected intraperitoneally with saline solution (0.01 cc/g of body weight) and processed as described above.

Still another group of 20 mice is injected intraperitoneally with 0.125 mg/kg of physostigmine and processed as described above.

Results of this test on a representative compound of the present invention is reported in Table II.

TABLE II

| Hypoxic Survival Test | | |
|---|---|---|
| Compound | Dose mg/kg | Percent Survivors |
| 7,8-Dihydro-8-(3-(trifluoromethyl)-phenyl)-3$\underline{H}$,6$\underline{H}$-1,4,5a,8a-tetraazaacenaphthylene-3,5(4$\underline{H}$)-dione | 100 | 60 |

Another in vivo test associated with decreased neural function in mammals is the Passive Avoidance Anoxic Induced Amnesia Test. This test is used to determine the attenuation of anoxic induced amnesia in mice treated with a drug, as compared to saline treated control animals with no drug.

A shock-motivated, single trial, step-through passive avoidance procedure is used. Groups of 25 Swiss-Webster, middle-aged mice (9 months of age) are placed singly in the front chamber of a 2-chamber box and are allowed to voluntarily cross into the rear chamber. As soon as the mouse enters the rear chamber, a door automatically traps the animal and a mild electric shock (0.4 mA for 4 seconds) is delivered to its feet. Following the foot shock, the mice are initially placed in an anoxic environment (0 percent oxygen) for 12 seconds, which quickly induces unconsciousness. They are then placed in a hypoxic environment (15 percent oxygen) for four minutes which prolongs the oxygen deprived state, maintaining unconsciousness. All testing is performed 24 hours later, and in all cases the mice appear fully recovered from the previous anoxic/hypoxic treatment. All test compounds are administered intraperitoneally at a dose of 10–200 mg/kg, 30 minutes prior to training and testing. Control animals are injected intraperitoneally only with saline at 0.01 cc/g of body weight.

The latency to enter the rear chamber is recorded for both training and testing. Presumably, the more the animal remembers being shocked, the greater it will inhibit going into the rear chamber and the higher will be its latency to re-enter. An improvement of 30 percent over saline control scores is considered active. The result of this test on a representative compound of the present invention appears in Table III.

TABLE III

| Passive Avoidance Anoxic Induced Amnesia Test | | |
|---|---|---|
| Compound | Dose mg/kg | Percent Improvement |
| 4-Methyl-8-(3-(trifluoromethyl)-phenyl)-3$\underline{H}$,6$\underline{H}$-1,4,5a,8a-tetraazaacenaphthylene-3,5(4$\underline{H}$)-dione | 100 | 79 |

The novel compounds of the present invention have been found to be highly useful for lowering elevated blood pressure in mammals when administered in amounts ranging from about 2.0 mg to about 100 mg/kg of body weight per day. A preferred dosage regimen for optimum results would be from about 50 mg to about 750 mg per dose. Such dosage units are employed so that a total of from about 200 mg to about 3.0 g of the active compound, for a subject of about 70 kg of body weight, is administered in a 24 hour period.

The compounds of the present invention have been found to be useful for the treatment of cognitive and related neural behavioral problems in mammals when administered in amounts ranging from about 5 mg to about 20 mg/kg of body weight per day. A preferred dosage regimen for optimum results would be from about 10 mg to about 50 mg/kg of body weight per day and such dosage units are employed so that a total of from about 700 mg to about 3.5 g of the active compound for a subject of about 70 kg of body weight is administered in a 24 hour period.

The hereinabove described dosage regimen for lowering elevated blood pressure and treating neural behavioral problems in mammals may be adjusted to provide the optimum therapeutic response. For example, several divided doses may be administered daily or the dose may be proportionally reduced as indicated by the exigencies of the therapeutic situation. A decided practical advantage is that these active compounds may be administered in any convenient manner such as by the oral, intravenous, intramuscular or subcutaneous routes.

The active compounds may be orally administered, for example, with an inert diluent or with an assimilable edible carrier, or they may be enclosed in hard or soft shell gelatin capsules, or they may be compressed into tablets or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1 percent of active compound. The percentage of the compositions and preparations may, of course, be varied and may conveniently be between about 2 percent to about 60 percent of the weight of the unit. The amount of active compound in such therapeutically useful compositions is such that a suitable dosage will be obtained. Preferred compositions or preparations according to the present invention are prepared so that an oral dosage unit form contains between about 5 and 200 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

DESCRIPTION OF THE PREFERRED EMBODIMENTS

The following examples illustrate the present invention. They are not to be construed to limit the claims in any manner whatsoever.

EXAMPLE 1

7-(3-(Trifluoromethyl)phenyl)pyrazolo(1,5-a)-pyrimidine-3 carboxamide

A mixture of 3.0 g of 7-(3-trifluoro-methyl) phenyl)-pyrazolo(1,5-a)pyrimidine-3-carbonitrile (prepared as described in U.S. Pat. No. 4,236,005) and 150 ml of concentrated sulfuric acid is stirred at room temperature for 4 hours. The solution is then carefully poured into ice water with stirring. The white precipitate which forms is collected, washed with water and then with saturated sodium bicarbonate until the washes are neutral. The solid is heated with one liter of isopropyl alcohol and filtered. The white solid is dried in vacuo and gives the product of the example as a colorless solid, mp 256–258° C.

EXAMPLE 2

7-(2,5-Dichlorophenyl)-2-methylpyrazolo(1,5-a)-pyrimidine-3-carboxamide

A mixture of 31.0 g of 2',5'-dichloroacetophenone and 25 ml of N,N-dimethylformamide dimethyl acetal is heated on a steam bath for 6 hours, then evaporated to dryness in vacuo. The residue is slurried with hexane, filtered, and gives 35.3 g of 2', 5'-dichloro-3-dimethylaminoacrylophenone as orange crystals, mp 83–85° C.

A mixture of 12.2 g of 3-amino-4-cyano-5-methyl-pyrazole and 24.4 g of 2',5'-dichloro-3-dimethylaminoacrylophenone in 250 ml of glacial acetic acid is heated on a steam bath for 4 hours. The mixture is cooled and filtered and gives 21.28 g of 7-(2,5-dichlorophenyl)-2-methyl-pyrazolo(1,5-a)pyrimidine-3-carbonitrile as off-white crystals.

The 21.28 g of the preceding product is dissolved in concentrated sulfuric acid and stirred for 5 hours. The solution is carefully poured onto ice. The precipitate which forms is collected by filtration, washed with water and dried to give the product of the example as colorless crystals, mp 234–236° C.

EXAMPLES 3–7

Additional pyrazolo(1,5-a)pyrimidine-3-carboxamides which are prepared from the corresponding pyrazolo(1,5-a)pyrimidine-3-carbonitriles in the manner described in Example 1 are listed in Table IV.

TABLE IV

Pyrazolo(1,5-a)pyrimidime-3-carboxamides

| EXAMPLE | COMPOUND | R$_2$ | R$_3$ | MP °C. |
|---|---|---|---|---|
| 3 | 7-Phenylpyrazolo(1,5-a)-pyrimidine-3-carboxamide | H | phenyl | 236–238.5 |
| 4 | 2-Methyl-7-phenylpyrazolo-(1,5-a)pyrimidine-3-carboxamide | CH$_3$ | phenyl | 233–235 |
| 5 | 7-(3-Pyridinyl)pyrazolo-(1,5-a)pyrimidine-3-carboxamide | H | 3-pyridinyl | 285–286 |
| 6 | 7-(4-Pyridinyl)pyrazolo-(1,5-a)pyrimidine-3-carboxamide | H' | 4-pyridinyl | 394–396 |

TABLE IV-continued
Pyrazolo(1,5-a)pyrimidine-3-carboxamides

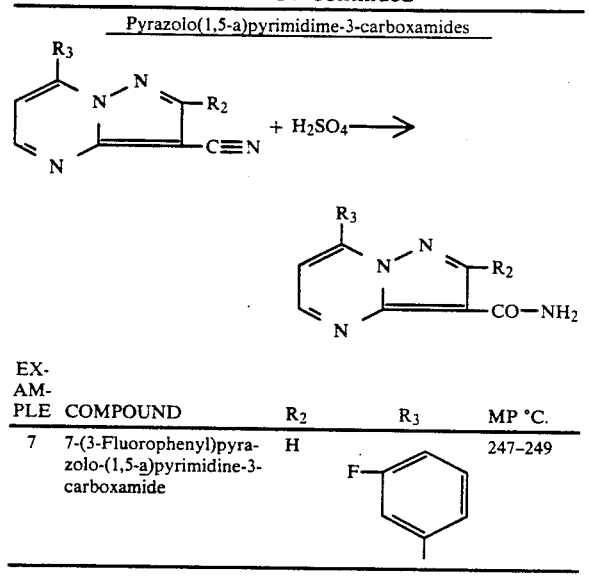

| EX-AMPLE | COMPOUND | R$_2$ | R$_3$ | MP °C. |
|---|---|---|---|---|
| 7 | 7-(3-Fluorophenyl)pyrazolo-(1,5-a)pyrimidine-3-carboxamide | H | 3-F-C$_6$H$_4$- | 247–249 |

EXAMPLE 8

4,5-Dihydro-7-(3-(trifluoromethyl)phenyl)-pyrazolo(1,5 -a)pyrimidine-3-carboxamide A 10.0 g amount of 7-(3-(trifluoromethyl) phenyl)-pyrazolo(1,5-a)pyrimidine-3-carboxamide (prepared in the manner described in Example 1) is stirred under nitrogen as a suspension in 120 ml of glacial acetic acid (cooled in an ice bath) and then 5.5 g of sodium cyanoborohydride is added to the reaction mixture in portions with an additional 80 ml of glacial acetic acid. After one hour of stirring in the ice bath the mixture is stirred at room temperature for 19 hours. The solution is evaporated to dryness, then water is added and the white precipitate which forms is collected by filtration and washed with an aqueous saturated solution of sodium bicarbonate, then with water. The solid is treated with 100 ml of acetonitrile, isolated and dried to give 5.25 g of the desired product, which is recrystallized from acetonitrile, mp 157–160° C.

EXAMPLE 9

7-(2,5-Dichlorophenyl)-4,5-dihydro-2-methyl-pyrazolo(1,5-a)pyrimidine-3-carboxamide A 3.21 g portion of 7-(2,5-dichlorophenyl)-2methyl-pyrazolo(1,5-a)pyrimidine-3-carboxamide (Example 2) is suspended in 150 ml of glacial acetic acid and stirred under nitrogen at room temperature. Then 1.5 g of sodium cyanoborohydride is added in portions and stirring is continued for 3 hours. The reaction mixture is evaporated to dryness in vacuo and when water is added to the residue a white precipitate forms. This solid is collected and dissolved in dichloromethane, and this solution is washed with an aqueous saturated solution of sodium bicarbonate. Then the organic phase is dried over anhydrous sodium sulfate and filtered. The filtrate is evaporated in vacuo and gives 2.95 g of the product of this example as a white solid, mp 93–96° C.

EXAMPLE 10

4,5-Dihydro-7-(3-pyridinyl)pyrazolo(1,5-a)-pyrimidine-3-carboxamide

A 20.0 g amount of 7-(3-pyridinyl)pyrazolo-(1,5-a)pyrimidine-3-carboxamide (prepared as described in Example 5) is suspended in 200 ml of glacial acetic acid with stirring under nitrogen at room temperature. Then 14 g of sodium cyanoborohydride is added in portions and the mixture is stirred for 3 hours. The mixture is allowed to stand at room temperature for 16 hours, and then the reaction mixture is evaporated to dryness. Water is added, followed by saturated sodium bicarbonate until pH 8.0 is achieved and a gummy solid precipitates. The solid is collected by filtration and dissolved in acetonitrile. The acetonitrile is evaporated and gives 10.0 g of yellow solid (A). The aqueous filtrate above is evaporated to dryness and extracted with acetonitrile. Evaporation gives a yellow gummy solid (8). Solids (A) and (B) are combined and triturated with isopropyl alcohol. A yellow solid is isolated and dried in vacuo to give 6.19 g of the desired product which is recrystalized from isopropanol-acetonitrile, mp 182–184° C.

EXAMPLE 11

7-(3-Fluorophenyl)-4,5 dihydropyrazolo(1,5 -a)-pyrimidine-3-carboxamide

A 136.3 g amount of 7-(3-fluorophenyl)-pyrazolo(1,5-a)pyrimidine-3-carboxamide (prepared as described in Example 7) in one liter of glacial acetic acid is stirred at room temperature, then 83.6 g of sodium cyanoborohydride is added portionwise under nitrogen. The mixture is stirred for 16 hours, then the precipitated crystals are collected by filtration and triturated with saturated sodium bicarbonate until pH 7–8 is achieved. The crystals are washed with water and dried in vacuo to give 63.0 g of the product as cream colored crystals, mp 122–125° C.

EXAMPLE 12

4,5-Dihydro 7-(3-(trifluoromethyl)phenyl)pyrazolo-(1,5-a)pyrimidine-3-carboxylic acid, ethyl ester To a 20.0 g amount of 7-(3-(trifluoromethyl)-phenyl)-pyrazolo(1,5-a)pyrimidine-3-carboxylic acid, ethyl ester (U.S. Pat. No. 4,178,449, Example 16) stirred in 100 ml of glacial acetic acid and cooled in a water bath is added portionwise 10.0 g of sodium cyanoborohydride under nitrogen. The mixture is stirred at room temperature for 3 hours. Evaporation of the mixture in vacuo gives an oil which solidifies on treatment with water. This solid is collected by filtration and is then stirred with a saturated solution of sodium bicarbonate, then is filtered, washed with water and dried in vacuo to give a white solid. Recrystallization from isopropyl alcohol gives 18.2 g of the desired product, mp 108–110° C.

EXAMPLE 13

4,5,6,7-Tetrahydro-7-(3-(trifluoromethyl)Phenyl)-pyrazolo(1,5-a)pyrimidine-3-carboxamide A solution of 3.44 g of 4,5-dihydro-7-(3-trifluoromethyl)phenyl)pyrazolo(1,5-a)pyrimidine-3-carboxamide (Example 8) in 40 ml of trifluoroacetic acid is stirred under nitrogen and heated to 60° C. in an oil bath. Then 5.0 ml of triethylsilane is added and the mixture is stirred at 60° C. for 24 hours. The reaction mixture is cooled and carefully poured into a beaker containing a 25 percent aqueous solution of potassium hydroxide and cracked ice. The product which precipitates is extracted into chloroform, and the extract is washed with water, dried over anhydrous sodium sulfate and filtered.

The filtrate is evaporated in vacuo to give crystals which are then recrystallized from toluene-hexane to give the desired product, mp 152–154° C.

EXAMPLE 14

8-(3-(Trifluoromethyl)phenyl)-3H,6H-1,4,5a,8a-tetraazaacenaphthylene-3,5(4H)-dione To a stirred mixture of 10.0 g of 4,5-dihydro-7-(3-(trifluoromethyl)phenyl)pyrazolo(1,5-a)pyrimidine-3-carboxamide (prepared as described in Example 8) in 200 ml of dioxane at room temperature under nitrogen is added 20.0 g of 1,1'-carbonyldiimidazole. The mixture is then heated at reflux for 5 hours, and then is cooled and filtered. The filtrate is evaporated to dryness in vacuo and an excess of water is added to the residue. The white solid which forms is collected and is recrystallized from acetonitrile-ethanol to give 6.5 g of the desired product as a white solid, mp 260–262° C.

EXAMPLE 15

7,8-Dihydro-8-(3-(trifluoromethyl)phenyl)-3H,6H-1,4,5a,8a-tetraazaacenaphthylene-3,5(4H)-dione To a 3.0 g portion of 4,5,6,7-tetrahydro-7-(3-(trifluoromethyl)phenyl)pyrazolo(1,5-a)pyrimidine-3-carboxamide (Example 13) suspended in 40 ml of dry tetrahydrofuran is added portionwise under nitrogen 8.0 g of 1,1'-carbonyldiimidazole and 60 ml of dry tetrahydrofuran. The reaction mixture is heated at reflux for 96 hours, and then is cooled to give a white precipitate which is collected by filtration. The precipitate is treated with 10 ml of water, filtered and dried to give 1.05 g of the desired product as a white solid, mp 297–300° C.

EXAMPLE 16

8-(2,5-Dichlorophenyl)-2-methyl-3H,6H-1,4,5a,8a-tetraazaacenaphthylene-3,5(4H)-dione To a 3.0 g amount of 7-(2,5-dichlorophenyl)-4,5-dihydro-2-methylpyrazolo(1,5-a)pyrimidine-3-carboxamide (Example 9) suspended and stirred in 100 ml of dry p-dioxane, under nitrogen is added 8.0 g of 1,1'-carbonyldiimidazole. The mixture is evaporated to dryness in vacuo and the residue is treated with water to decompose the excess 1,1'-carbonyldiimidazole. The remaining solid is collected by filtration, then stirred with 50 ml of tetrahydrofuran. The solid is collected and dried to give 1.6 g of the desired product as a white solid. The product is recrystallized from ethanol-acetonitrile and gives mp 205–209° C.

EXAMPLE 17

4-Methyl-8-(3-(trifluoromethyl)phenyl)-3H,6H,1,4,5a,8a-tetraazaacenaphthylene-3,5(4H)-dione To a stirred mixture of 2.0 g of 8-(3-(trifluoromethyl)phenyl)-3H,6H-1,4,5a,8a-tetraazaacenaphthylene-3,5-(4H)-dione (Example 14) in 20 ml of N,N-dimethylformamide, under nitrogen is added 270 mg of 60 percent sodium hydride. The mixture is stirred at room temperature for 3 hours to form the anion, and then 0.5 ml of methyl iodide is added to the stirred mixture through a hypodermic syringe. After stirring for 3 hours at room temperature an additional 0.5 ml of methyl iodide is added and stirring is continued for 16 hours. The mixture is poured into water and the white precipitate which forms is collected, washed with water and dried in vacuo. Recrystallization from isopropyl alcohol gives 1.5 g of the desired product as a white solid, mp 190–192° C.

In a like manner, 1-iododecane is added to the above anion to give 4-decyl-8-(3-(trifluoromethyl)phenyl)-3H,6H-1,4,5a,8a-tetraazaacenaphthylene-3,5(4H)-dione.

EXAMPLE 18

8-(3-Pyridinyl)-3H,6H-1,4,5a,8a-tetraazaacenaphthylene-3,5(4H)-dione

A mixture of 4.0 g of 4,5-dihydro-7-(3-pyridinyl)-pyrazolo(1,5-a)pyrimidine-3-carboxamide (Example 10), 80 ml of dry p-dioxane and 10.0 g of 1,1'-carbonyldiimidazole is heated at reflux for 5 hours. Then an additional 5.0 g of 1,1'-carbonyldiimidazole is added and heating is continued for 16 hours. After cooling to room temperature the precipitated solid is collected by filtration, washed with water and dried in vacuo to give 2.0 g of the desired product as a white solid, mp 292–295° C.

EXAMPLE 19

4-(4-Chlorophenyl)-8-(3-trifluoromethyl)-phenyl)3H,6H-1,4,5a,8a tetraazaacenaphthylene-3,5(4H)-dione A mixture of 5.0 g of 4,5-dihydro-7-(3-(trifluoromethyl)phenyl)pyrazolo(1,5-a)pyrimidine-3-carboxylic acid, ethyl ester (Example 12) and 2.5 g of p-chlorophenyl isocyanate in 40 ml of toluene is heated at reflux for 16 hours. The reaction mixture is evaporated to dryness in vacuo and water is added to the residue. This mixture is extracted with chloroform, and the organic phase is separated, dried over anhydrous sodium sulfate and filtered. Evaporation of the filtrate gives 8.51 g of a yellow oil which is triturated with diethyl ether to precipitate a white solid. The solid is collected and dried in vacuo to give 2.0 of 4-(((4-chlorophenyl) amino)carbonyl)-4,5-dihydro-7-(3-(trifluoromethyl)-phenyl)-pyrazolo(1,5-a)pyrimidine-3-carboxylic acid, ethyl ester, mp 163–165° C.

A 1.0 g portion of the preceding compound in 20 ml of 5 percent aqueous sodium hydroxide is stirred and heated in an oil bath at 120° C. for 3 hours. The reaction mixture is cooled to room temperature and a white solid forms. The solid is collected, washed with water and then with glacial acetic acid. The product is dried in vacuo and gives 700 mg of the desired product as a light yellow solid which is recrystallized from toluene, mp 177–180° C.

EXAMPLE 20

3,5-Dioxo-8-(3-(trifluoromethyl)phenyl)-3H,6H-1,4,5a,-8a-tetraazaacenaphthylene-3,5(4H)-acetamide To a stirred mixture of 5.0 g of 8-(3-(trifluoromethyl)phenyl)-3H,6H-1,4,5a,8a-tetraazaacenaphthylene-3,5(4H)-dione (prepared as described in Example 14) in 50 ml of dry N,N-dimethylformamide, under nitrogen, is added 800 mg of 60 percent sodium hydride (dispersion in mineral oil). The mixture is stirred at room temperature for 2 hours. Then 3.4 g of 2-iodoacetamide is added and stirring is continued for 48 hours. The reaction mixture is evaporated to dryness, then treated with water. The solid precipitate is collected by filtration and dried to give 5.0 g of the desired product as a white solid. The product is recrystallized from acetonitrile-N,N-dimethylformamide-water, mp 282–284° C.

EXAMPLE 21

4-Ethyl-8-(3-(trifluoromethyl)phenyl)-3H,6H-1,4,5a,8a-tetraazaacenaphthylene-3,5(4H)-dione To a stirred mixture of 5.0 g of 8-(3-(trifluoromethyl)-phenyl)-3H,6H-1,4,5a,8a-tetraazaacenaphthylene-3,5(4H)-dione (prepared as described in Example 14) in 50 ml of dry N,N-dimethylformamide, under nitrogen, is added 800 mg of 60 percent sodium hydride (dispersion in mineral oil). The mixture is stirred at room temperature for 2 hours, then 10 ml of iodoethane is added and stirring is continued for 48 hours. The reaction mixture is evaporated to dryness, then treated with water, and the gummy solid which is isolated is dissolved in chloroform and the extract dried over anhydrous sodium sulfate. Evaporation gives an oil which is triturated with diethyl ether-hexane to provide a yellow solid which is collected by filtration to give 2.0 g of the desired product as a white solid. The product is recrystallized from isopropyl alcohol, mp 161–163° C.

EXAMPLE 22

4-((4-Nitrophenyl)methyl)-8-(3-(trifluoromethyl)-phenyl)-3H,6H-1-4,5a,8a-tetraazaacene-3,5-(4H)-dione To a stirred mixture of 5.0 g of 8-(3-(trifluoromethyl)-phenyl)-3H,6H-1,4,5a,8a-tetraazaacenaphthylene-3,5(4H)-dione (prepared as described in Example 14) in 50 ml of dry N,N-dimethylformamide, under nitrogen, is added 800 mg of 60 percent sodium hydride (dispersion in mineral oil). The mixture is stirred at room temperature for 2 hours, then 3.3 g of 4-nitrobenzyl bromide in 10 ml of N,N-dimethylformamide are added and the mixture is stirred at room temperature for 40 hours. The mixture is evaporated to dryness in vacuo, then treated with water to give a tan solid. The solid is collected by filtration, washed with water and dried. The solid is dissolved in dichloromethane and passed through a short column of magnesium silicate. The eluate is evaporated in vacuo to give 5.9 g of the desired product as a light yellow solid. The product is recrystallized from isopropyl alcohol-ethyl acetate, mp 184–186° C.

EXAMPLE 23

4-(Phenylmethyl)-8-(3-(trifluoromethyl)phenyl)3H,6H-1,4,5a,8a-tetraazaacenaphthylene 3,5(4H)-dione To a stirred mixture of 4.0 g of 8-(3-(trifluoromethyl)-phenyl)-3H,6H-1,4a,8a-tetraazaacenaphthylene3,5(4H)-dione (prepared as described in Example 14) in 40 ml of dry N,N-dimethylformamide, under nitrogen, is added 650 mg of 60 percent sodium hydride (dispersion in mineral oil). The mixture is stirred at room temperature for 2 hours, then 2.5 g of benzyl bromide is added and the mixture is stirred for 40 hours.

The mixture is evaporated to dryness in vacuo, then treated with water to give a white precipitate which is collected, washed with water and air dried. The solid is dissolved in chloroform and the solution is dried over anhydrous sodium sulfate and filtered. The filtrate is evaporated in vacuo and gives 7.0 g of an oil which is triturated with diethyl ether-hexane to give a white solid. The solid is collected, dissolved in a small amount of hot toluene and filtered through magnesium silicate. Hexane is added to the filtrate until a white precipitate forms. The mixture is cooled on ice, then filtered to collect the desired product. The material is dried and gives 1.5 g as a white solid, mp 144–146° C.

EXAMPLE 24

4,5-Dihydro-5-thioxo-8-(3-(trifluoromethyl)phenyl)-3H,6H-1,4,5a,8a-tetraazaacenaphthylene-3-one To a stirred solution of 1.00 g of 4,5-dihydro-7-(3-(trifluoromethyl)phenyl)pyrazolo(1,5-a)pyrimidine-3-carboxamide (prepared as described in Example 8) in 30 ml of dry tetrahydrofuran cooled to −78° C. is added 286 mg of 60 percent sodium hydride (dispersion in mineral oil). The reaction mixture is stirred at −78° C. for 30 minutes then 637 mg of 1,1′-thiocarbonyldiimidazole is added and the mixture is allowed to slowly warm to room temperature and then is stirred for 36 hours. The mixture is quenched with water, neutralized with 5 percent aqueous hydrochloric acid and extracted with chloroform. Evaporation of the extract in vacuo gives 934 mg of the desired product.

EXAMPLE 25

5-(Methylthio)-8-(3-(trifluoromethyl)phenyl)-3H,6H-1,4,5a,8a-tetraazaacenaphthylen-3-one To a solution of 100 mg of 4,5-dihydro-5-thioxo-8-(3-(trifluoromethyl)phenyl)-3H,6H-1,4,5a,8a-tetraazaacenaphthylen-3-one (Example 24) in 10 ml of dry tetrahydrofuran, cooled at 0° C., is added 13 mg of sodium hydride (60 percent dispersion in mineral oil). The reaction mixture is stirred at 0° C. for 15 minutes, then an excess of methyl iodide is added and the mixture is allowed to warm to room temperature and then is stirred for 3 hours. The mixture is quenched with water and extracted with chloroform and evaporation of the extract in vacuo gives 47 mg of the desired product mp 234–237° C. (with decomposition).

EXAMPLE 26

4,5-Dihydro-8-phenyl-5-thioxo-3H,6H-1,4,5a,8a-tetraazaacenaphthylen-3-one

A mixture of 7.6 g of 4,5-dihydro-7-phenyl-pyrazolo(1,5-a)pyrimidine-3-carboxamide (prepared as described in Example 25 of commonly assigned U.S. Pat. No. 4,847,256) in 304 ml of dry tetrahydrofuran is stirred and cooled at −78° C., under nitrogen and 2.17 g of sodium hydride (60 percent dispersion in mineral oil) is added. The mixture is stirred at −78° C. for 30 minutes, then 4.84 g of 1,1′-thiocarbonyldiimidazole is added in one portion and the temperature is kept at −78° C. for 2 hours and then is allowed to rise slowly to room temperature. Stirring is continued for 48 hours, and then the reaction mixture is quenched with 500 ml of water and neutralized with 5 percent aqueous hydrochloric acid. A crystalline solid forms which is collected by filtration, triturated with ether, filtered and dried to give 3.2 g of the desired product as white crystals, mp 289–291° C.

EXAMPLE 27

8-(3-Fluorophenyl)-4,5-dihydro-5-thioxo-3H,6H-1,4,5a,8a-tetraazaacenaphthylen-3-one A mixture of 63.0 g of 7-(3-fluorophenyl)-4,5-dihydropyrazolo(1,5-a)pyrimidine-3-carboxamide (Example 11) and 2.5 liters of dry tetrahydrofuran is stirred and cooled to −78° C. in a dry ice-acetone bath, then 18.0 g of sodium hydride (60 percent dispersion in mineral oil) is added in one portion This mixture is stirred at −78°

C. for 1.5 hours then 40.0 g of 1,1'-thiocarbonyldiimidazole is added and stirring is continued at −78° C. for 2 hours. The mixture is allowed to warm to room temperature and is stirred for 48 hours and then the reaction is quenched with 2.5 liters of water and neutralized with 5 percent aqueous hydrochloric acid. The crystalline solid that forms is collected, washed with ether and dried to give 54.6 g of the desired product as cream colored crystals, mp 298–300° C.

EXAMPLES 28-30

A 2-methyl-3-dimethylaminoacrylophenone is reacted with 3-amino-4-cyanopyrazole in glacial acetic acid according to the procedures described in commonly assigned U.S. Pat. No. 4,236,005 to give the corresponding 6-methyl-7-(substituted phenyl)-pyrazolo-(1,5-a)pyrimidine-3-carbonitrile, set forth below in Table V.

TABLE V

| EXAMPLE | 2-METHYL-3-DIMETHYL-AMINOACRYLOPHENONE | RESULT | MELTING POINT, °C. |
|---|---|---|---|
| 28 | 3'-trifluoromethyl | 6-methyl-7-((3-trifluoromethyl)phenyl)pyrazolo(1,5-a)pyrimidine-3-carbonitrile | 158–160 |
| 29 | 4'-chloro | 6-Methyl-7-(4-chlorophenyl)-pyrazolo(1,5-a)pyrimidine-3-carbonitrile | 161–163 |
| 30 | 3'-chloro | 6-Methyl-7-(3-chlorophenyl)-pyrazolo(1,5-a)pyrimidine-3-carbonitrile | 206–208 |

EXAMPLE 31

6-Methyl-7-(3-(trifluoromethyl)phenyl)pyrazolo-(1,5-a)pyrimidine-3-carboxamide

A mixture of 27.6 g of 6-methyl-7-((3-trifluoromethyl)phenyl)pyrazolo(1,5-a)pyrimidine-3-carbonitrile and 175 ml of concentrated sulfuric acid is stirred at room temperature for 4 hours. The solution is then carefully poured into ice water with stirring. The white precipitate which forms is collected, washed with water and then with saturated sodium bicarbonate until the washes are neutral. The solid is heated with one liter of isopropyl alcohol and filtered. The resulting white solid is dried in vacuo to give the product of the example as a colorless solid, mp 237–239° C.

EXAMPLES 32-33

The procedure of Example 31 is repeated to hydrolyze a 6,7-disubstituted pyrazolo(1,5-a)pyrimidine-3-carbonitrile to the corresponding carboxamide. The results are set forth below in Table VI.

TABLE VI

| EXAMPLE | CARBONITRILE | CARBOXAMIDE | MP °C. |
|---|---|---|---|
| 32 | 6-Methyl-7-(4-chlorophenyl)-pyrazolo(1,5-a)pyrimidine-3-carbonitrile | 6-Methyl-7-(4-chlorophenyl)pyrazolo(1,5-a)pyrimidine-3-carboxamide | 276–277 |
| 33 | 6-Methyl-7-(3-chlorophenyl)pyrazolo(1,5-a)pyrimidine-3-carbonitrile | 6-Methyl-7-(3-chlorophenyl)pyrazolo(1,5-a)pyrimidine-3-carboxamide | 211–213 |

EXAMPLE 34

4,5-Dihydro-6-methyl-7-(3-(trifluoromethyl)phenyl-pyrazolo(1,5-a)pyrimidine-3-carboxamide An 18.7 g amount of 6-methyl-7-(3-trifluoromethyl)-phenyl)pyrazolo(1,5-a)pyrimidine-3-carboxamide (prepared as described in Example 31) is stirred under nitrogen as a suspension in 200 ml of glacial acetic acid (cooled in an ice bath) and then 3.67 g of sodium cyanoborohydride is added to the reaction mixture in portions. After one hour of stirring in the ice bath, the mixture is stirred at room temperature for 4.5 hours. The solution is evaporated to dryness, then water is added and the solid which forms is collected by filtration and washed with an aqueous saturated solution of sodium bicarbonate, then with water. The product is then recrystallized from ethyl acetate-hexane to give 16.2 g of the desired product, mp 200–202° C.

EXAMPLES 35-36

The procedure of Example 34 is repeated to reduce a 6,7-disubstituted pyrazolo(1,5-a)pyrimidine to the corresponding 4,5-dihydro-6,7-disubstituted pyrazolo(1,5-a)pyrimidine. The results are set forth in Table VII below.

TABLE VII

| EXAMPLE | PYRAZOLO(1,5-a)PYRIMIDINE | 4,5-DIHYDROPYRAZOLO(1,5-a)PYRIMIDINE | MP °C. |
|---|---|---|---|
| 35 | 6-Methyl-7-(4-chlorophenyl)pyrazolo(1,5-a)pyrimidine-3-carboxamide | 4,5-Dihydro-6-methyl-7-(4-chlorophenyl)pyrazolo((1,5-a)pyrimidine-3-carboxamide | 210–212 |
| 36 | 6-Methyl-7-(3-chlorophenyl)-pyrazolo(1,5-a)pyrimidine-3-carboxamide | 4,5-Dihydro-6-methyl-7-(3-chlorophenyl)-pyrazolo(1,5-a)pyrimidine-3-carboxamide | 197–20(' |

EXAMPLE 37

8-((3-Trifluoromethyl)phenyl)-4,5-dihydro-7-methyl-5-thioxo-3H,6H-1,4,5a,8a-tetraazaacenaphthylen-3-one A mixture of 5.0 g of 7-((3-trifluoromethyl) phenyl)-4,5-dihydro-6-methylpyrazolo(1,5-a)pyrimidine-3carboxamide (Example 34) and 0.2 liters of dry tetrahydrofuran is stirred and cooled to −78° C. in a dry ice-acetone bath, then 1.43 g of sodium hydride (60 percent dispersion in mineral oil) is added in one portion. This mixture is stirred at −78° C. for 1.5 hours, then 3.19 g of 1,1 '-thiocarbonyldiimidazole is added and stirring is continued at −78° C. for 2 hours. The mixture is allowed to warm to room temperature and is stirred for 48 hours, and then the reaction is quenched with 0.5 liters of water and neutralized with 5 percent aqueous hydrochloric acid. The crystalline solid that forms is collected, washed with ether and dried to give 4.0 g of the desired product as cream colored crystals, mp 269-271° C.

EXAMPLE 38

8-(4-Chlorophenyl)-4,5-dihydro-7-methyl-5-thioxo-3H, 6H-1,4,5a,8a-tetraazaacenaphthylen-3 one A mixture of 5.0 g of 7-(4-chlorophenyl)-4,5-dihydro-6-methylpyrazolo(1,5-a)pyrimidine-3-carboxamide (Example 35) and 0.2 liters of dry tetrahydrofuran is stirred and cooled to −78° C. in a dry ice-acetone bath, then 1.43 g of sodium hydride (60 percent dispersion in mineral oil) is added in one portion. This mixture is stirred for 0.5 hours, then 3.19 g of 1,1 '-thiocarbonyldiimidazole is added and stirring is continued at −78° C. for 2 hours. The mixture is allowed to warm to room temperature and is stirred for 48 hours and then the reaction is quenched with 0.5 liters of water and neutralized with 5 percent aqueous hydrochloric acid. The crystalline solid that forms is collected, washed with ether and dried to give 4.2 g of the desired product as cream colored crystals, mp. 283-285° C.

EXAMPLE 39

8-(3-Chlorophenyl)-4,5-dihydro-7-methyl-5-thioxo-3H, 6H-1,4,5a,8a-tetraazaacenaphthylen-3-one A mixture of 5.0 g of 7-(3-chlorophenyl)-4,5-dihydro-6-methylpyrazolo(1,5-a)pyrimidine-3-carboxamide (Example 36) and 0.2 liters of dry tetrahydrofuran is stirred and cooled to −78° C. in a dry ice-acetone bath, then 1.43 g of sodium hydride (60 percent dispersion in mineral oil) is added in one portion. This mixture is stirred at −78° C. for 1.5 hours then 3.19 g of 1,1'-thiocarbonyldiimidazole is added and stirring is continued at −78° C. for 2 hours. The mixture is allowed to warm to room temperature and is stirred for 48 hours and then the reaction is quenched with 0.5 liters of water and neutralized with 5 percent aqueous hydrochloric acid. The crystalline solid that forms is collected, washed with ether and dried to give 4.0 g of the desired product as cream colored crystals, mp 289-291° C.

The above mentioned patents, patent applications and publications are incorporated herein by reference.

Many variations of the present invention will suggest themselves to those skilled in this art in light of the above detailed description. All such obvious modifications are within the full intended scope of the appended claims.

We claim:

1. A compound selected from the group consisting of those of the formulae:

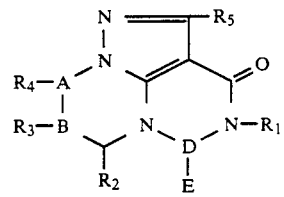

A or

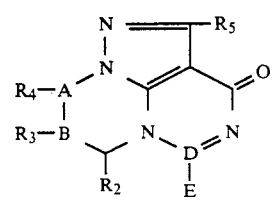

B or a pharmaceutically acceptable salt thereof, wherein $R_1$ is selected from the group consisting of hydrogen, alkyl having from 1 to 10 carbon atoms, carboxamidomethyl, 4-chlorophenyl, benzyl and (4-nitrophenyl)methyl; $R_2$ and $R_3$ are hydrogen or alkyl having from 1 to 3 carbon toms; $R_4$ is 3-pyridinyl or

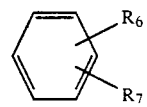

where $R_6$ and $R_7$ may be the same or different and are selected from the group consisting of hydrogen, halogen, alkyl having from 1 to 3 carbon atoms, N-alkyl-N-acylamino where both alkyl and acyl have from 1 to 3 carbon atoms, nitro, and trifluoromethyl and where halogen is selected from chlorine, bromine, fluorine and iodine; $R_5$ is hydrogen or alkyl having from 1 to 10 carbon atoms; A-B may be

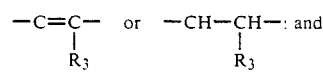

wherein in Formula A D-E represents C=X where X is oxygen or sulfur; or wherein in Formula B D-E represents C—$SR_8$ where $R_8$ is alkyl having from 1 to 3 carbon atoms.

2. A compound selected from the group consisting of the formula

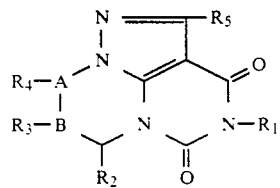

or a pharmaceutically acceptable salt thereof, wherein $R_1$ is selected from the group consisting of hydrogen, alkyl having from 1 to 10 carbon atoms, carboxamidomethyl, 4-chlorophenyl, benzyl and (4-nitrophenyl)methyl; $R_2$ and $R_3$ are hydrogen or alkyl having from 1 to 3 carbon atoms; $R_4$ is 3-pyridinyl or

where $R_6$ and $R_7$ may be the same or different and are selected from hydrogen, halogen, alkyl having from 1 to 3 carbon atoms, alkoxy having from 1 to 3 carbon atoms, N-alkyl-N-acylamino where both alkyl and acyl have from 1 to 3 carbon atoms, nitro, and trifluoromethyl and where halogen is selected from chlorine, fluorine, bromine and iodine; $R_5$ is hydrogen or alkyl having from 1 to 10 carbon atoms; and A-B is

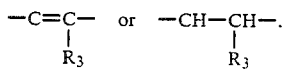

3. A compound as defined in claim 1 which is 7-(3-(trifluoromethyl)phenyl-3H,6H-1,4,5a,8a-tetraazaacenaphthylene-3,5(4H)-dione or a pharmaceutically acceptable salt thereof.

4. A compound as defined in claim 1 which is 7,8-dihydro-8-(3-(trifluoromethyl)phenyl)-3H,6H-1,4,5a,8a-tetraazaacenaphthylene-3,5(4H)-dione or a pharmaceutically acceptable salt thereof.

5. A compound as defined in claim 1 which is 8-(2,5-dichlorophenyl)-2-methyl-3H,6H-1,5a,8a-tetraazaacenaphthylene-3,5(4H)-dione or a pharmaceutically acceptable salt thereof.

6. A compound as defined in claim 1 which is 4-methyl-8-(3-(trifluoromethyl)phenyl)-3H, 6H-1,4,5a,8a-tetraazaacenaphthylene-3,5(4H)-dione.

7. A compound as defined in claim 1 which is 8-(3-pyridinyl)-3H,6H-1,4,5,a,8a-tetraazaacenaphthylene-3,5(4H)-dione or a pharmaceutically acceptable salt thereof.

8. A compound as defined in claim 1 which is 4-(4-chlorophenyl)-8-(3-(trifluoromethyl)phenyl)-3H,6H-1,4,5a,8a-tetraazaacenaphthylene-3,5(4H)-dione.

9. A compound as defined in claim 1 which is 8-(3-(trifluoromethyl)phenyl)-3H,6H-1,4,5a,8a-tetraazaacenaphthylene-3,5(4H)-dione or a pharmaceutically acceptable salt thereof.

10. A compound as defined in claim 1 which is 4-ethyl-8-(3-(trifluoromethyl)phenyl)-3H,6H-1,4,5a,8a-tetraazaacenaphthylene-3,5(4H)-dione.

11. A compound as defined in claim 1 which is 4-((4-nitrophenyl)methyl)-8-(3-(trifluoromethyl)phenyl)-3H,6H-1,4,5a,8a-tetraazaacenaphthylene-3,5(4H)-dione.

12. A compound as defined in claim 1 which is 4-(phenylmethyl)-8-(3-(trifluoromethyl)phenyl)-3H,6H-1,4,5a,8a-tetraazaacenaphthylene-3,5(4H)-dione.

13. A therapeutic composition for treating hypertension in humans and other mammals, comprising from about 5 to about 250 mg of a compound as defined in claim 1, in combination with a pharmaceutically acceptable carrier or diluent.

14. A therapeutic composition as defined in claim 13 in dosage unit form.

15. A therapeutic composition as defined in claim 14 in the form of tablets, pills, capsules, ampoules or sachets.

16. A nootropic composition for treating cognitive disorders in humans and other mammals, comprising from about 50 to about 250 mg of a compound as defined in claim 1, in combination with a pharmaceutically acceptable carrier or diluent.

17. A nootropic composition as defined in claim 16 in dosage unit form.

18. a nootropic composition as defined in claim 15 in the form of tablets, pills, capsules elixirs, suspensions, syrups or wafers.

19. A method of lowering elevated blood pressure in humans or other mammals which comprises administering to said human or other mammal an effective hypotensive amount of a compound selected from those of the formulae:

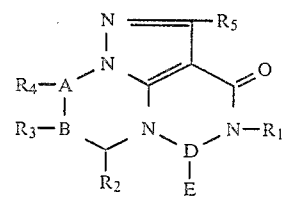 A or

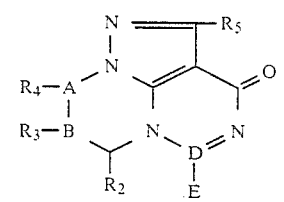 B or a pharmaceutically acceptable salt thereof, wherein $R_1$ is selected from the group consisting of hydrogen, alkyl having from 1 to 10 carbon atoms, carboxamidomethyl, 4-chlorophenyl, benzyl and (4-nitrophenyl)methyl; $R_2$ and $R_3$ are hydrogen or alkyl having from 1 to 3 carbon atoms; $R_4$ is 3-pyridinyl or

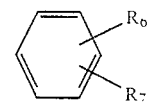

where $R_6$ and $R_7$ may be the same or different and are selected from hydrogen, halogen, alkyl having from 1 to 3 carbon atoms, alkoxy having from 1 to 3 carbon atoms, N-alkyl-N-acylamino where both alkyl and acyl have from 1 to 3 carbon atoms, nitro and trifluoromethyl, and where halogen is selected from chlorine, bromine, fluorine and iodine; $R_5$ is hydrogen or alkyl having from 1 to 10 carbon atoms; A-B is

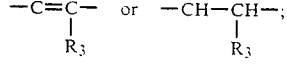

and wherein in Formula A D-E represents C=X where X is oxygen or sulfur; or wherein in Formula B D-E represents C—SR$_8$ where R$_8$ is alkyl having from 1 to 3 carbon atoms.

20. A method of treating cognitive and related neural behavioral problems in humans and other warm blooded animals which comprises administering internally to said humans and other warm blooded animals an effective amount of a compound selected from those of the formulae:

A

B or a pharmaceutically acceptable salt thereof, wherein R₁ is selected from the group consisting of hydrogen, alkyl having from 1 to 10 carbon atoms, carboxamidomethyl, 4-chlorophenyl, benzyl and (4-nitrophenyl)methyl; R₂ and R₃ are hydrogen or alkyl having from 1 to 3 carbon atoms, R₄ is 3-pyridinyl or where R₆ and R₇ are the same or different and are selected from hydrogen, halogen, alkyl having from 1 to 3 carbon atoms, alkoxy having from 1 to 3 carbon atoms, N-alkyl-N-acylamino where both alkyl and acyl have from 1 to 3 carbon atoms, nitro and trifluoromethyl, and where halogen is selected from chlorine, bromine, fluorine and iodine; R₅ is hydrogen or alkyl having from $$-\underset{R_3}{C}=C- \quad \text{or} \quad -\underset{R_3}{CH}-CH-;$$

1 to 10 carbon atoms; A-B may be $$-\underset{R_3}{C}=C- \quad \text{or} \quad -\underset{R_3}{CH}-CH-;$$

and wherein in Formula A D-E represents C=X where X is oxygen or sulfur; or wherein in Formula B D-E represents C—SR₈ where R₈ is alkyl having from 1 to 3 carbon atoms.

21. A compound of the formulae:

A

B or a pharmaceutically acceptable salt thereof, wherein R₁ is selected from the group consisting of hydrogen, alkyl having from 1 to 10 carbon atoms, carboxamidomethyl, 4-chlorophenyl, benzyl and (4-nitrophenyl)methyl; R₂ and R₃ are hydrogen or alkyl having from 1 to 3 carbon atoms, R₄ is 3-pyridinyl or where R₆ and R₇ may be the same or different and are selected from the group consisting of hydrogen, halogen, alkyl having from 1 to 3 carbon atoms, alkoxy having from 1 to 3 carbon atoms. N-alkyl-N-acylamino where both alkyl and acyl have from 1 to 3 carbon atoms, nitro and trifluoromethyl, and where halogen is selected from chlorine, bromine, fluorine and iodine. R₅ is hydrogen or alkyl having from 1 to 10 carbon atoms, A-B is $$-\underset{R_3}{C}=C- \quad \text{or} \quad -\underset{R_3}{CH}-CH-; \text{ and}$$

wherein in Formula A D-E represents C=X where X is sulfur; or wherein in Formula B D-E represents C—SR₈ where R₈ is alkyl having from 1 to 3 carbon atoms.

22. A compound as defined in claim 21 wherein R₁ is hydrogen.

23. A composition as defined in claim 1 which is 4,5-dihydro-5-thioxo-8-(3-(trifluoromethyl)phenyl)-3H, 6H-1,4,5a,8a-tetraazaacenaphthylene-3-one.

24. A composition as defined in claim 1 which is 5-(methylthio)-8-(3-(trifluoromethyl)phenyl)-3H, 6H-1, 4,5a,8a-tetraazaacenaphthylen-3-one.

25. A composition as defined in claim 1 which is 4,5-dihydro-8-phenyl-5-thioxo-3H,6H-1,4,5a,8a-tetraazaacenaphthylen-3one.

26. A composition as defined in claim 1 which is 8-(3-fluorophenyl)-4,5-dihydro-5-thioxo-3H,6H-1,4,5a, 8a-tetraazaacenaphthylene-3-one.

* * * * *